United States Patent [19]

Guthöhrlein et al.

[11] 4,206,200

[45] Jun. 3, 1980

[54] STABILIZER FOR POLYSACCHARIDES

[75] Inventors: Gerhard Guthöhrlein; Torsten B. Helting, both of Marburg an der Lahn, Fed. Rep. of Germany

[73] Assignee: Behringwerke Aktiengesellschaft, Marburg an der Lahn, Fed. Rep. of Germany

[21] Appl. No.: 954,461

[22] Filed: Oct. 25, 1978

[30] Foreign Application Priority Data

Oct. 27, 1977 [DE] Fed. Rep. of Germany ....... 2748132

[51] Int. Cl.² .............................................. A61K 39/02
[52] U.S. Cl. ...................................................... 424/92
[58] Field of Search ............................................ 424/92

[56] References Cited

U.S. PATENT DOCUMENTS

| | | | |
|---|---|---|---|
| 2,908,614 | 10/1959 | Muggleton et al. | 424/92 |
| 3,135,663 | 6/1964 | Muggleton et al. | 424/92 |
| 3,322,632 | 5/1967 | Schwick et al. | 424/92 |
| 3,532,790 | 10/1970 | Greenberg et al. | 424/92 |
| 3,567,585 | 3/1971 | Bloch et al. | 424/92 |
| 3,577,527 | 5/1971 | Edwards | 424/92 |
| 3,599,150 | 8/1971 | Feinberg et al. | 424/92 |
| 3,608,066 | 9/1971 | Illartein | 424/92 |
| 3,636,192 | 1/1972 | Gotschlich | 424/92 |
| 3,743,720 | 7/1973 | Fosker et al. | 424/92 |
| 3,859,434 | 1/1975 | Jennings et al. | 424/92 |

OTHER PUBLICATIONS

Tiesjema, R. H. et al., Chem. Abstr. 87:122686v (1977) of Bull. W.H.O. (1977), 55(1), 43–48, "Enhanced Stability of Meningococcal Polysaccharide Vaccines by Using Lactose as a Menstruum for Lyophilization".

*Primary Examiner*—Shep K. Rose
*Attorney, Agent, or Firm*—Curtis, Morris & Safford

[57] ABSTRACT

For improving the stability of menningococcal polysaccharides in aqueous solution, lactose is completely or partially replaced by another compound which forms a hydrate and can be reversibly dehydrated under the conditions of lyophilization. The mixture may then be dried and/or processed to a vaccine.

7 Claims, No Drawings

STABILIZER FOR POLYSACCHARIDES

The invention relates to a stabilizer for meningococcal-polysaccharides. In particular, the invention relates to the stabilization of meningococcal-capsule-polysaccharides of group A. If further relates to the preparation of a vaccine against meningococcal diseases which contains stabilized meningococcal-polysaccharides.

The known vaccines against meningitis caused by meningococci contain as the essential active components group-specific polysaccharides which can be isolated from meningococci of the serological groups A and C. The polysaccharides are isolated from miningococcal cultures and purified by various precipitation and extraction measures (cf. E. C. Gotschlich et al., Progr. immunbiol. Standard., Vol. 5, pp. 485–491, Karger, Basel, 1972 and WHO Technical Report Ser. No. 594, and pages 66/67, 1976).

Meningococcal-polysaccharides and the vaccines prepared therefrom often exhibit unsatisfactory stability during storage, which affects the immunizing effect of the active substances. Even in the dry, i.e. lyophilized state, the miningococcal-vaccines show an extraordinary instability. Even with a water content of less than 1% in the dry mass, the material hydrolyzes to a detectable degree in the course of some months when stored at about 4° C., and at higher temperatures within one week. Therefore, miningococcal-polysaccharides are generally stored in the deep-frozen state.

The hydrolysis of the meningococcal-polysaccharides leads to a depolymerization and results in an undesirable reduction of the immunogenicity of the vaccine which contains them. The depolymerization can be detected by determining the change in the molecular weight by chromatography.

It is known from investigations made by the Rijks Institut voor the Volkgezondheid, Bilthoven, Bull.Wdl.Hlth. Org., 55, 43–48 , 1977, that lactose considerably improves the stability during storage of meningococcal-polysaccharides. An explanation for the increase in the stability of lactose over that caused by the hitherto used but unsatisfactory mannitol could not be given.

Now, we have found that, surprisingly, hydrate-forming compounds which are dehydrated under the conditions of lyophilization and subsequently hydrate reversibly, are capable of stabilizing meningococcal-polysaccharides.

In particular, these compounds are sucrose, raffinose, glucose, trehalose, glycerophosphate and glutaminate as well as lactose. Sucrose and raffinose are preferred, either alone or in admixture with one of the other mentioned compounds. With the exception of lactose alone, they form the subject matter of the invention as stabilizers for meningococcal-polysaccharides.

For stabilization, at least 0.3 mg, preferably 1 to 100 mg, of the compounds are added for about 100/μof meningococcal-polysaccharides in aqueous solution. The mentioned quantities by weight are contained in about 1 ml of an aqueous solution suitable as a vaccine.

Thus, the subject of the invention is an improvement in the stabilization of meningococcal polysaccharides by the addition of lactose, which comprises adding to the aqueous solution of the meningococcal polysaccharide, instead of the total amount or a part of lactose, at least 0.3 mg, for 100/μg of polysaccharide, of at least one compound which forms a hydrate and can be reversibly dehydrated under lyophilization conditions, and drying the mixture obtained.

In a preferred embodiment the mixture is subsequently lyophilized. The aqueous solution of the meningococcal-polysaccharides thus stabilized may represent either an intermediate product for the preparation of a vaccine or a vaccine preparation suitable for parenteral administration.

It is another object of the invention to provide a vaccine containing meningococcal-polysaccharides which contains also sucrose, raffinose, glucose, trehalose, glycerophosphate or glutaminate, optionally in admixture with lactose.

It is still another object of the invention to use sucrose, raffinose, glucose, trehalose, glycerophosphate, or glutaminate, optionally in admixture with lactose, as stabilizer for meningococcal-polysaccharides, for example those of the group A.

In a preferred embodiment of the invention, at least one of the stabilizing compounds is used in a concentration of 5 to 20 mg/ml of the vaccine solution to be administered. If the content of stabilizer is too high, for example with sucrose over 100 mg per ml, hypertonic solutions result so that it is not suitable to exceed this concentration in the case of parenteral administration of a corresponding polysaccharide vaccine.

Although, the compounds of the invention impart to the meningococcal-polysaccharide an excellent stability after lyophilization of the solution, it may sometimes be suitable not to use the stabilizers alone but together with other compounds to stabilize the meningococcal-polysaccharides. Such mixtures sometimes show a synergistic effect and further improve the stability during storage of the meningococcal-polysaccharides. Such a synergism is observed in particular in the case of mixtures of two of the mentioned stabilizers in a molar ratio of 1:2 to 2:1.

For preparing the meningococcal-polysaccharides it is suitable to proceed according to WHO Technical Report Ser. No. 594, pages 66/67, 1976, as follows:

A meningococcal culture or its culture supernatant is combined with 0.1 to 0.3% of cetyltrimethylammonium bromide (=Cetavlon$^{(R)}$) and the precipitate is isolated after 2–24 hours by sedimentation or centrifugation. The sediment is subsequently extracted with a 0.8–2 molar, preferably 1 molar, aqueous solution of calcium chloride, combined with up to 20–30%, preferably 25% (v/v) of ethanol and the supernatant is isolated by centrifugation. The intermediate product is precipiated by further addition of up to 70–85%, preferably 80% (v/v) of ethanol and then isolated by centrifugation.

The intermediate product is then taken up in a neutral to weakly basic aqueous medium, for example a 0.1–0.4 M sodium acetate solution and then extracted with phenol. A buffer-saturated phenol solution is used (composition: 100 g of phenol +40 ml of buffer). The aqueous phase is dialyzed against 0.1 M calcium chloride solution and subjected to ultracentrifugation. The polysaccharide is then precipitated with the aid of an alcohol, preferably ethanol and dried. The material is stored at −20° C. At least one stabilizing compound, optionally with other additives, is then added to the redissolved meningococcal-polysaccharide obtained as described above and the mixture is lyophilized.

Such a product, processed into a vaccine, is the main object of the invention.

It has, for example, the following composition:

| 1. N. meningitidis group A polysaccharide | 2.5 mg |
|---|---|
| Sucrose | 250 mg |

During storage for 3 months at 37° C., the lyophilized product showed practically no decrease in the degree of polymerization. The Kd-value which was 0.26 when first stored rose to 0.29. In comparison, a sample stabilized with lactose under the same conditions showed an increase of the Kd-value from 0.26 to 0.35.

For the administration as vaccine, the lyophilisate is dissolved in 25 ml of a physiologically tolerated solvent. For this purpose, a solution is used which contains: 7 mg of NaCl/ml; 0.015 mol/l of sodium phosphate buffer, pH 7.4, 0.05 mg of sodium timerfonate/ml.

| 2. N. meningitidis group A polysaccharide | 2.5 mg |
|---|---|
| Lactose | 125 mg |
| Sucrose | 125 mg |

During storage of the lyophilized material at 56° C., the Kd-value of the polysaccharide rose within 2 months from 0.26 to 0.48. Products combined with 250 mg of lactose or 250 mg of sucrose showed after the same period of time Kd-values of >0.7.

$K_d$ is determined by chromatography on Sepharose$^{(R)}$ 4 B and is defined by the following equation:

$$k_d = (V_e - V_o / V_T - V_o)$$

$V_e$ = The volume of the eluate from the start of the chromatography to the elution maximum of the main component of the polysaccharide antigen.

$V_o$ = The elution volume of a totally excluded substance, for example high molecular Blue Dextrane.

$V_T$ = The elution volume of a totally included substance, for example radio-actively labelled water.

This definition means that $0 \leq K_d \leq 1$. The limit values are reached with a completely excluded substance ($K_d = 0$) or with a completely included substance ($K_d = 1$). With a higher Kd-value, the size of the molecule is reduced. In the present case, a rising $K_d$-value indicates that the meningococcal-polysaccharide depolymerizes.

What is claimed is:

1. In a process for improving the stabilization of a Neisseria Meningitidis polysaccharide by the addition of lactose, the improvement comprising adding to an aqueous solution of *Neisseria meningitidis* polysaccharide, instead of the total amount of a part of lactose, at least 0.3 mg per 100 μg of *Neisseria meningitidis* polysaccharide of at least one compound selected from the group consisting of sucrose, raffinose, glucose, trehalose, glycerophosphate and glutaminate as a stabilizer to increase the stabilization of *Neisseria meningitidis* and which stabilizer forms a hydrate and can be reversibly dehydrated under conditions of lyophilization.

2. The process of claim 1 wherein 1 to 100 mg per 100 μg of polysaccharide of at least one stabilizer is added.

3. In the process of claim 1 wherein an aqueous reconstituted solution of freeze-dried *Neisseria meningitidis* polysaccharide is suitable for parenteral administration.

4. A *Neisseria meningitidis* vaccine comprising an aqueous solution of *Neisseria meningitidis* polysaccharide and at least 0.3 mg per 100 μg of polysaccharide of a stabilizer selected from the group consisting of sucrose, raffinose, glucose, trehalose, glycerophosphate and glutaminate.

5. A vaccine according to claim 4 wherein the *Neisseria meningitidis* polysaccharide is in admixture with lactose.

6. A vaccine according to claims 4 or 5 wherein the stabilizer is present in an amount of 5 to 20 mg/ml of the vaccine solution.

7. A method for stabilizing a *Neisseria meningitidis* polysaccharide which comprises adding at least 0.3 mg per 100 μg of *Neisseria meningitidis* of a stabilizer selected from the group consisting of sucrose, raffinose, glucose, trehalose, glycerophosphate and glutaminate to an aqueous solution of a *Neisseria meningitidis* polysaccharide.

* * * * *